(12) United States Patent
Moe et al.

(10) Patent No.: US 9,498,194 B2
(45) Date of Patent: Nov. 22, 2016

(54) SURGICAL INSTRUMENT INPUT DEVICE ORGANIZATION SYSTEMS AND ASSOCIATED METHODS

(71) Applicant: University of Washington through its Center for Commercialization, Seattle, WA (US)

(72) Inventors: Kristen S. Moe, Seattle, WA (US); Randall Bly, Seattle, WA (US); Blake Hannaford, Seattle, WA (US)

(73) Assignee: University of Washington, Seattle, WA (US)

( * ) Notice: Subject to any disclaimer, the term of this patent is extended or adjusted under 35 U.S.C. 154(b) by 155 days.

(21) Appl. No.: 14/255,779

(22) Filed: Apr. 17, 2014

(65) Prior Publication Data

US 2014/0313172 A1    Oct. 23, 2014

Related U.S. Application Data

(60) Provisional application No. 61/813,091, filed on Apr. 17, 2013.

(51) Int. Cl.
| | | |
|---|---|---|
| *A61B 19/00* | (2006.01) | |
| *G06F 3/02* | (2006.01) | |
| *A61B 17/00* | (2006.01) | |

(52) U.S. Cl.
CPC ............. *A61B 17/00* (2013.01); *A61B 34/74* (2016.02); *A61B 2017/00207* (2013.01); *A61B 2017/00221* (2013.01); *A61B 2017/00973* (2013.01)

(58) Field of Classification Search
CPC ............. G06F 3/0334; G06F 19/3406; A61B 17/00; A61B 2017/00973; A61B 2019/2269; A61B 18/00; A61B 34/25; A61B 34/74; A61B 2017/00221
USPC ........ 345/156–173, 184; 600/102, 125, 126; 606/1, 34–40
See application file for complete search history.

(56) References Cited

U.S. PATENT DOCUMENTS

| | | |
|---|---|---|
| 4,933,843 A | 6/1990 | Scheller et al. |
| 5,300,926 A | 4/1994 | Stoeckl |
| 5,422,521 A | 6/1995 | Neer et al. |
| 6,260,434 B1 | 7/2001 | Holtorf |
| 7,781,941 B2 | 8/2010 | Horvath et al. |
| 7,896,869 B2 | 3/2011 | DiSilvestro et al. |
| 8,075,317 B2 | 12/2011 | Youngblood |
| 2002/0115917 A1* | 8/2002 | Honda .............. A61B 17/00 600/301 |
| 2004/0169673 A1 | 9/2004 | Crampe et al. |
| 2005/0049458 A1* | 3/2005 | Honda .............. A61B 1/0005 600/118 |
| 2005/0080403 A1* | 4/2005 | Takahashi .......... A61B 17/00 606/1 |

(Continued)

*Primary Examiner* — Hong Zhou
(74) *Attorney, Agent, or Firm* — Perkins Coie LLP (57) ABSTRACT

Organization systems for surgical instruments input devices and associated methods and systems are disclosed herein. In one aspect, a surgical instrument input device organization system can include a first interface configured to receive input from a user and a second interface communicatively coupled to the first interface via a link. The second interface can include a module sized to receive a surgical input instrument device and an actuator configured to engage a movable surface of the surgical instrument input device in response to input received from the user at the first interface.

24 Claims, 6 Drawing Sheets

(56) References Cited

U.S. PATENT DOCUMENTS

| | | | | |
|---|---|---|---|---|
| 2006/0217700 A1* | 9/2006 | Garito | A61B 18/12 | 606/34 |
| 2009/0157093 A1* | 6/2009 | Van Dalen | A61F 9/0133 | 606/130 |
| 2009/0316193 A1* | 12/2009 | Kohara | G03G 15/5016 | 358/1.15 |
| 2010/0100080 A1 | 4/2010 | Huculak et al. | | |
| 2011/0125149 A1* | 5/2011 | El-Galley | A61B 17/00 | 606/34 |

* cited by examiner

SURGICAL INSTRUMENT INPUT DEVICE ORGANIZATION SYSTEMS AND ASSOCIATED METHODS

CROSS-REFERENCE TO RELATED APPLICATION(S)

This application claims the benefit of U.S. Provisional Application No. 61/813,091, filed Apr. 17, 2013, and incorporated herein by reference in its entirety.

TECHNICAL FIELD

The present technology relates generally to systems and methods for organizing instrument input devices and/or controls. In particular, several embodiments are directed to systems configured to organize instrument input devices (e.g., pedals, controls, switches, toggles, etc.) for use in hospital rooms and/or other medical operating environments.

BACKGROUND

Many surgical procedures require multiple surgical instruments (e.g., endoscopes, microdebriders, sonopets, coblators) each coupled to a corresponding pedal and/or input device via a cable or wire. Multiple pedals of different sizes and shapes may be used throughout a surgical procedure. Furthermore, many surgical instruments are proprietary and operating rooms therefore are usually equipped with pedals from a variety of manufacturers. In the course of a typical surgical procedure, one or more pedals may be transferred between a surgeon and an assistant. The assistant can operate a surgical instrument using a pedal for a period of time, and subsequently transfer the pedal to the surgeon or vice versa. The transfer of pedals can lead to tangling of cables attached to different pedals, which in turn may cause difficulty in locating a desired pedal. Often, an assistant has to crawl under an operating table to detangle the resulting mess of cables, leading to unnecessary and potentially life-threatening delays during a surgical procedure. Accordingly, there exists a need for a system to organize surgical instrument input devices and cables in a medical environment.

DETAILED DESCRIPTION

The present technology relates generally to surgical instrument input device organization systems and associated methods. For example, in one embodiment of the present technology, a surgical instrument input device organization system includes a first interface configured to receive input from an operator and a second interface communicatively coupled to the first interface via a link. The second interface can include one or more modules each sized to receive a surgical input instrument device. At least one of the modules can include an actuator configured to engage a movable surface (e.g., a pedal) of the surgical instrument input device in response to input received from the user at the first interface.

In some embodiments, the actuator can include an end portion configured to engage the movable surface with a predetermined amount of pressure. Actuating the movable surface can change an orientation of the movable surface relative to the end portion of the actuator from between a first orientation and at least a second orientation. The input device can be configured to selectively activate and deactivate a corresponding surgical instrument based on the orientation of the movable surface.

In some embodiments, the first interface can include a surface configured to receive input from a foot of the user. The surface can have a proximal portion configured to receive a first portion of the user's foot and a plurality of distal portions configured to receive touch input from an a second, different portion of the user's foot. The first surface can have any suitable shape such as, for example, a rectangle, a square, a triangle, an ellipse, a circle, and/or a circular sector. In some embodiments, the first interface can also include a camera configured to track a position of at least a portion of a foot of the user. The second interface can also include a first receptacle and a second receptacle each sized to receive a plug electrically connected to a surgical instrument input device. The first and second receptacles can include first and second input ports, respectively. The first input port can be sized to receive a first plug from a first surgical instrument input device, and the second input port is sized to receive a second plug from a second surgical instrument input device different from the first input device.

In another embodiment of the present technology, a surgical instrument input device organization system can include a user interface configured to receive input from an operator; and an enclosure configured to hold a plurality of modules. The individual modules can be configured to receive a corresponding surgical input instrument device and can include an actuator communicatively coupled to the user interface and positioned at least proximate the corresponding surgical instrument input device. The actuator can be configured to engage a movable surface of a surgical instrument input device in response to input received from the operator. The actuator can be further configured to engage the movable surface (e.g., a pedal of a surgical instrument input device) with a predetermined amount of pressure to move the pedal from a first orientation to a second orientation. The input device can configured, for example, to provide an operating instruction to a corresponding surgical instrument when the movable surface is in the second orientation. In some embodiments of this aspect, the user interface can include a touchscreen, a microphone configured to receive voice input from an operator and/or a pressure-sensitive surface configured to receive foot input from the operator.

In yet another embodiment of the present technology, a surgical instrument input device organization system can include means for receiving input (e.g., a pedal, a pressure-sensitive mat, a touch sensitive surface, etc.) from a foot of a clinician, user and/or operator. The system can also include means for applying pressure (e.g., a mover, a motor and/or an actuator, such as a pneumatic or a hydraulic actuator) to a pedal of an input device coupled to a surgical instrument. In some embodiments of the third aspect, the means for applying pressure can be positioned remote from both the means for receiving input and the surgical instrument. The system can further include a link [e.g., a wire, a cable and/or a wireless connection using, for example, radio transmission (e.g., wifi), infrared transmission, optical transmission, etc.] configured to communicatively couple the means for receiving input to the means for applying pressure. The means for applying pressure can be configured change an orientation of the pedal from between a first orientation and a second orientation in response to input received from the clinician's foot via the link. In some embodiments, the means for receiving input from the clinician's foot can be configured to distinguish between a dorsiflexion and plantar flexion of the clinician's foot, between pronation and supination of the clinician's foot and/or between inversion and eversion of the clinician's foot.

Certain specific details are set forth in the following description and in FIGS. 1-6 to provide a thorough understanding of various embodiments of the technology. Other details describing well-known structures and systems often associated with surgical instruments and organization systems thereof have not been set forth in the following technology to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-6. Moreover, in the Figures, identical reference numbers identify identical, or at least generally similar, elements. To facilitate the discussion of any particular element, the most significant digit or digits of any reference number refers to the Figure in which that element is first introduced. For example, element 110 is first introduced and discussed with reference to FIG. 1.

Figure 1:
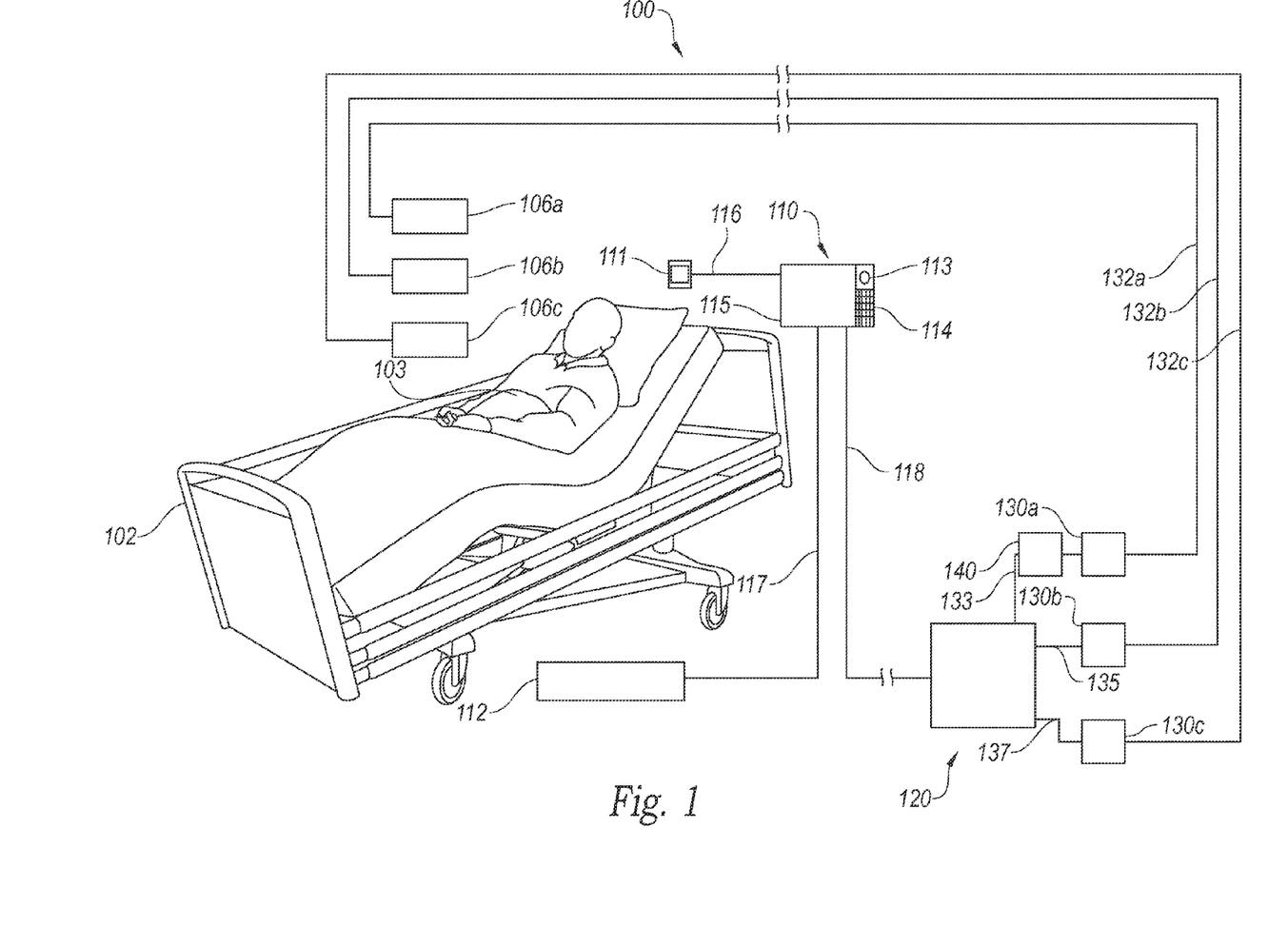
FIG. 1 is a partially schematic view of an instrument input device organization system configured in accordance with embodiments of the present technology.

FIG. 1 is a partially-schematic view of a surgical instrument input device organization system 100 configured in accordance with embodiments of the present technology. The system 100 is configured to organize input devices connected to corresponding surgical instruments in a surgical operating environment. Conventional operating environments can include several surgical instruments (e.g., endoscopes, cauteries, ablation devices, ultrasound devices, drills, lasers, debriding instruments, etc.) each having one or more input devices (e.g., pedals disposed on a floor near an operating table). Cables connecting the input devices to corresponding surgical instruments can easily tangle causing a jumble of pedals and cables.

As explained in further detail below, the system 100 can mitigate the tangling of input devices and cables by interfacing directly or indirectly with the input devices, allowing the input devices to be located remote from an operating table 102 (e.g., in the operating environment away from the operating table 102, in a room adjacent the operating environment and/or in a facility distant from a hospital housing the operating environment) holding a patient 103. As a result, the system 100 is expected to provide consolidation or reduced numbers of input device cables near or around the operating table 102.

The system 100 includes a user interface or first interface 110. In one aspect of the disclosed technology, the first interface 110 can comprise, for example, an input/output control system. The first interface 110 also includes a microphone 113, a speaker 114 and a display 115. The display 115 can comprise, for example, a touchscreen display configured to present a graphical user interface and/or receive touch input from one or more operators (e.g., one or more users, clinicians, surgeons, doctors and/or assistants). A sensor 111 (e.g., one or more sensors configured to determine a position, velocity and/or acceleration of one or more hands and/or feet of one or more operators) is communicatively coupled to the first interface 110 via a link 116 (e.g., a cable, a wire and/or wireless transmission). An input 112 (e.g., an input device configured to receive input from the one or more of the operators) is communicatively coupled to the first interface 110 via a link 117 (e.g., a cable, a wire and/or wireless transmission).

A hardware interface, input device interface or second interface 120 is communicatively coupled to the first interface 110 via a link 118 (e.g., a cable, a wire and/or wireless transmission). The second interface 120 can be configured to operate and/or transmit signals or instructions to one or more input devices to control one or more surgical instruments in response to input received from the operator at the first interface 110 and/or the input 112. In the illustrated embodiment, for example, the second interface 120 is communicatively coupled to a plurality of input devices 130 (identified separately as a first input device 130a, a second input device 130b and a third input device 130c) to correspondingly control one or more surgical instruments 106 (identified separately as a first instrument 106a, a second instrument 106b and a third instrument 106c) during a surgical procedure. A plurality of surgical instrument links 132 (e.g., identified separately as a first link 132a, a second link 132b and a third link 132c) communicatively couple the surgical instruments 106 to the corresponding input devices 130. The individual links 132 can include, for example, cables, wires and/or wireless transmission means.

A first link 133 (e.g., a cable, a wire and/or wireless transmission means) communicatively couples an actuator 140 to the second interface 120. As explained in further detail below in reference to FIGS. 3A-3C, the actuator 140 can be configured to actuate or move a control surface of the first input device 130a to change an orientation of the control surface (e.g., a pedal, toggle, switch, etc.) between a first orientation and at least a second orientation relative to the actuator 140 and/or the first input device 130a. A second link 135 (e.g., a cable, a wire and/or wireless transmission) communicatively couples the second input device 130b to the second interface 120. The second input device 130b may include, for example, a proprietary input device that has been configured to allow access to its wiring to provide direct control of a surgical instrument connected to the second input device 130b. A third link 137 (e.g., a cable, a wire and/or wireless transmission) communicatively couples the third input device 130c to the second interface via a receptacle (e.g., a plug and/or an adapter) (not shown in FIG. 1).

As described in more detail below in reference to FIG. 6, in some embodiments, the second interface 120 can include a plurality of receptacles each having an input port. The individual input ports can have different shapes and/or other characteristics (e.g., electrical characteristics such as polarity, voltage rating, current rating, etc.) and can each be configured to receive an output plug from a cable or wire connected to a surgical instrument. The receptacles can allow the second interface 120 to be coupled or connected to input devices having a variety of plugs and/or other coupling means. In the illustrated embodiment of FIG. 1, only the input devices 130*a-c* are shown. Those of ordinary skill in the art will recognize, however, that fewer or more than three devices can be communicatively coupled or otherwise connected to the second interface 120. Moreover, the second interface 120 can be positioned in any suitable location proximate the operating table 102 or distant from the operating table 102 (e.g., in the operating environment away from the operating table 102, in a room adjacent the operating environment and/or in a facility remote from a hospital housing the operating environment).

In the illustrated embodiment of FIG. 1, the input 112 is positioned on or near a floor surface at least proximate the operating table 102. The input 112 can include an input device (e.g., a pressure-sensitive or touch-sensitive mat or input surface) configured to receive foot input from a user. In some embodiments, for example, the input 112 can comprise a pedal device having several input regions. As described in further detail in reference to FIG. 4, pedal actions can be ergonomically incorporated into the input 112, and functions such as, for example, irrigation or cautery can be combined at a single input pedal. A separate switch can toggle between different types of functions. The pedal device can be activated in a number of ways, such as, for example, the user raising her foot, the user elevating her foot and/or a rocking action with dorsiflexion and plantar flexion. In further embodiments, the input 112 can comprise a wireless input device having several pedals that can be passed back and forth between a surgeon and an assistant without wires. Individual pedals can have dimensions, for example, approximately the size of a hockey puck (e.g., a disk having a diameter between about 5 cm and about 20 cm and a height between about 1 cm and 10 cm, a disk having a diameter between about 7 cm and about 12 cm and a height between about 1 cm and 10 cm, and/or a disk having a diameter of approximately 7.5 cm and a height of approximately 2.5 cm) and/or any other suitable size or shape. Moreover, individual surgical instruments can be assigned to each of the pedals and the pedals can be color coded accordingly. In yet further embodiments, the input 112 can comprise a multi-directional roller ball configured so that movement in one direction will trigger a specific task for a surgical instrument, while movement in a different device can trigger a different task for the same or a different surgical instrument.

In operation (e.g., during a surgical procedure) an operator associates one or more of the surgical instruments 106 with a corresponding input action (e.g., foot input received a predetermined input region at the input 112) via a graphical user interface (not shown) presented on the display 115 by the first interface 110. The input 112 can be configured to detect an input action (e.g., foot movements, foot movement patterns, foot gestures) corresponding to the surgical instrument 106 that the operator wishes to operate and/or activate. In response, the first interface 110 can provide instructions to the second interface 120 to activate the input device 130 communicatively coupled to the surgical instrument 106 corresponding to the detected input action. Activating the input device 130 may comprise, for example, actuating a control surface of the input device 130 (e.g., using the actuator 140) and/or transmitting one or more signals directly to the input device 130 and/or the surgical instrument 106. The system 100 is expected to perform the steps above without multiple pedals and, thus, multiple cables tangling during a surgical procedure.

Figure 2:
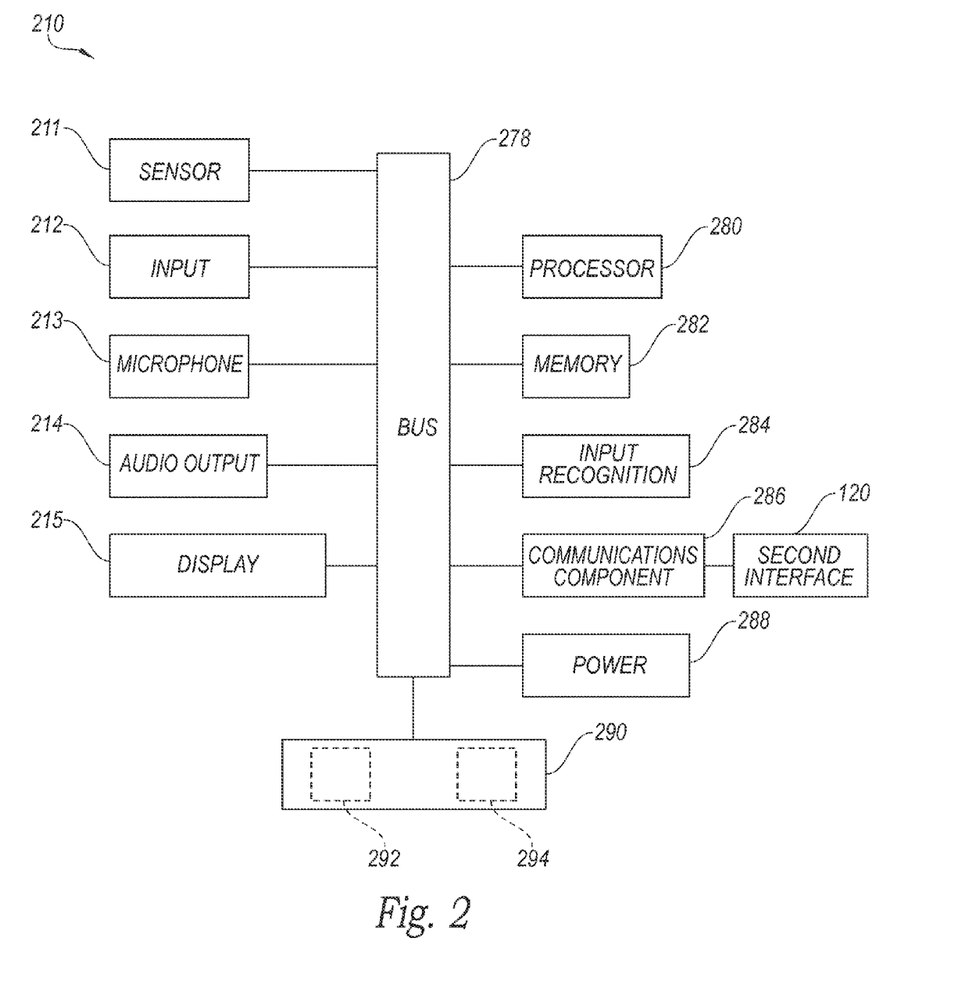
FIG. 2 is a schematic view of an input device organization system configured in accordance with another embodiment of the present technology.

FIG. 2 and the following discussion provide a brief, general description of a suitable environment in which the technology may be implemented. Although not required, aspects of the technology are described in the general context of computer-executable instructions, such as routines executed by a general-purpose computer (e.g., an ultrasound imaging device processing unit). Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network. In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In other embodiments, aspects of the technology may be distributed over the Internet or over other networks (including wireless networks), on a propagated signal on a propagation medium (e.g., an electromagnetic wave(s), a sound wave, etc.) over a period of time, or may be provided on any analog or digital network (packet switched, circuit switched, or other scheme).

Referring to FIG. 2, a block diagram illustrating example components of a user interface or interface 210 (e.g., the first interface 110 of FIG. 1) is shown. In the embodiment shown in FIG. 2, the interface 210 includes one or more sensors 211 (e.g., the sensor 111 of FIG. 1), an input 212 (e.g., one or more pedals, toggles, buttons, touchscreens, keyboards, trackballs, and/or other suitable input devices), a microphone 213 configured to receive voice input from a user, operator or clinician (e.g., a surgeon or doctor), an audio output 214 (e.g., a speaker), and a display 215 (e.g., one or more displays, one or more touchscreen displays, etc.). The interface 210 also includes a one or more processors 280, memory 282, an input recognition component 284, a communication component 286 and power 288.

In some embodiments, for example, the input 212 can be configured as a touch-sensitive and/or pressure sensitive surface (e.g., the input 112 of FIG. 1), a mat, one or more pedals and/or any other suitable device for receiving foot input. In other embodiments, the input 212 may be implemented as a touch-sensitive surface on the display 215. In further embodiments, the input 212 may include additional inputs such as, for example, inputs from a control panel, a keyboard, a trackball, a system accelerometer and/or pressure sensors in the touch screen, audio inputs (e.g., voice input received from the microphone 213), visual inputs, etc. In still further embodiments, the input 212 may be configured to receive non-tactile gestures performed by an operator without contacting a surface. In these embodiments, for example, the interface 210 can receive input from one or more of the sensors 211 (e.g., one or more cameras, one or more infrared transmitters and/or receivers, and/or one or more laser emitters and/or receivers configured to detect one or more operator foot or hand movements. The interface 210 can be configured to analyze the operator foot/hand movements and perform a corresponding action associated with the foot/hand movements. As described in further detail below with reference to FIG. 5, for example, the sensors 211 can include a camera positioned proximate an input surface (e.g., the input 112 of FIG. 1) and can track the movement of one or more feet of one or more operators. The interface 210 can be configured to perform one or more corresponding actions based on the visually-detected movements at the input surface. The sensor 211 can also be configured to detect a position, velocity and/or acceleration of one or more of the operator's hands and/or feet to determine one or more gestures and perform an action and/or selectively activate/deactivate a surgical instrument corresponding to the gesture(s).

The display 215 can be positioned, for example, in an operating room proximate an operating table (e.g., the operating table 102 of FIG. 1) and can be configured to display a graphical user interface to receive commands from an operator (e.g., a surgeon) and/or present a list, for example, of one or more surgical instruments. The graphical user interface, for example, may present a list of surgical instruments and another list of operator input actions (e.g., foot input locations and/or gestures received at the input 212) selected to activate and deactivate corresponding surgical instruments. The display 215 may include any suitable visual and/or audio display system such as, for example, a liquid crystal display (LCD) panel, a plasma-based display, a video projection display, etc. While only one display 215 is shown in FIG. 2, those of ordinary skill in the art would appreciate that multiple displays having similar or different outputs may be implemented in the interface 210.

The interface 210 may control components and/or the flow or processing of information or data between components using the one or more processors 280 in communication with the memory 282, such as ROM or RAM (and instructions or data contained therein) and the other components via a bus 278. The memory 260 may, for example, contain data structures or other files or applications that provide information related to the processing of input from the operator (e.g., foot input received from the input 212). The memory may also, for example, contain one or more instructions for providing an operating system and/or a graphical user interface presented on the display 215 and configured to display commands and receive input from the operator.

An input recognition component 284 coupled to the input 212 and the one or more processors 280 via the bus 278 can be configured to recognize and/or interpret input from the operator. The input recognition component 284 can be configured, for example, to disambiguate input received from a foot of the operator based on a relative motion of the operator's foot. For example, the input recognition component 284 may be configured to disambiguate between dorsiflexion and plantar flexion of the operator's foot, between pronation and supination of the operator's foot and/or between inversion and eversion of the operator's foot. In one embodiment, each of these movements of the operator's foot may be associated with a different action (e.g., functions associated with endoscope such as capture image, begin video recording, and/or adjustment of white balance) and/or a selective activation/deactivation of a desired surgical instrument. In other embodiments, the input recognition component 284 can receive input and determine a relative degree of adjustment (e.g., a zoom level of an endoscope) based on an intensity or movement of the operator's foot. In further embodiments, the input recognition component In further embodiments, the input recognition component 284 can be configured to determine a position of the operator's foot (e.g., two dimensional or X-Y coordinates and/or three-dimensional or X-Y-Z coordinates) based on input from the input 212.

In still further embodiments, the input recognition component 284 can be configured to disambiguate one or more movements of one or more of the operator's hands (e.g., by detecting a position, velocity and/or acceleration of the operator's hand(s)) to discern or otherwise recognize one or more gestures associated with one or more actions performed by a surgical instrument (e.g., one of the surgical instruments 106 of FIG. 1). For example, the input recognition component 284 can be configured to recognize hand movement associated with the operator's fist moving in a first direction and to recognize that hand movement associated with the operator's fist moving a second, different direction. As those of ordinary skill in the art will appreciate, however, the input recognition component 284 can also be configured to recognize any hand gesture (e.g., moving an open palm in a first direction, moving an open palm in a second direction, moving a first hand toward and/or away from a second hand, moving both hands toward each other, moving one or both hands in a circular direction, moving one or more individual fingers, etc.) and associate the gesture(s) with any suitable surgical instrument action (e.g., activating/deactivating a surgical instrument, zooming an endoscope in or out, moving a robotic arm of a surgical instrument, etc.)

Components of the interface 210 may receive energy via the power 288. Additionally, the interface 210 may receive or transmit information or data to other devices (e.g., the second interface 120 of FIG. 1), remote computing devices, and so on via the communication component 286. The communication component 286 can include any wired or wireless components capable of communicating data to and from the interface 210. Examples include a wireless radio frequency transmitter, infrared transmitter, or hard-wired cable, such as a USB cable. The interface 210 may include other additional components 290 having modules 292 and 294 not explicitly described herein, such as additional microprocessor components, removable memory components (flash memory components, smart cards, hard drives), and/or other components.

Figure 3A:
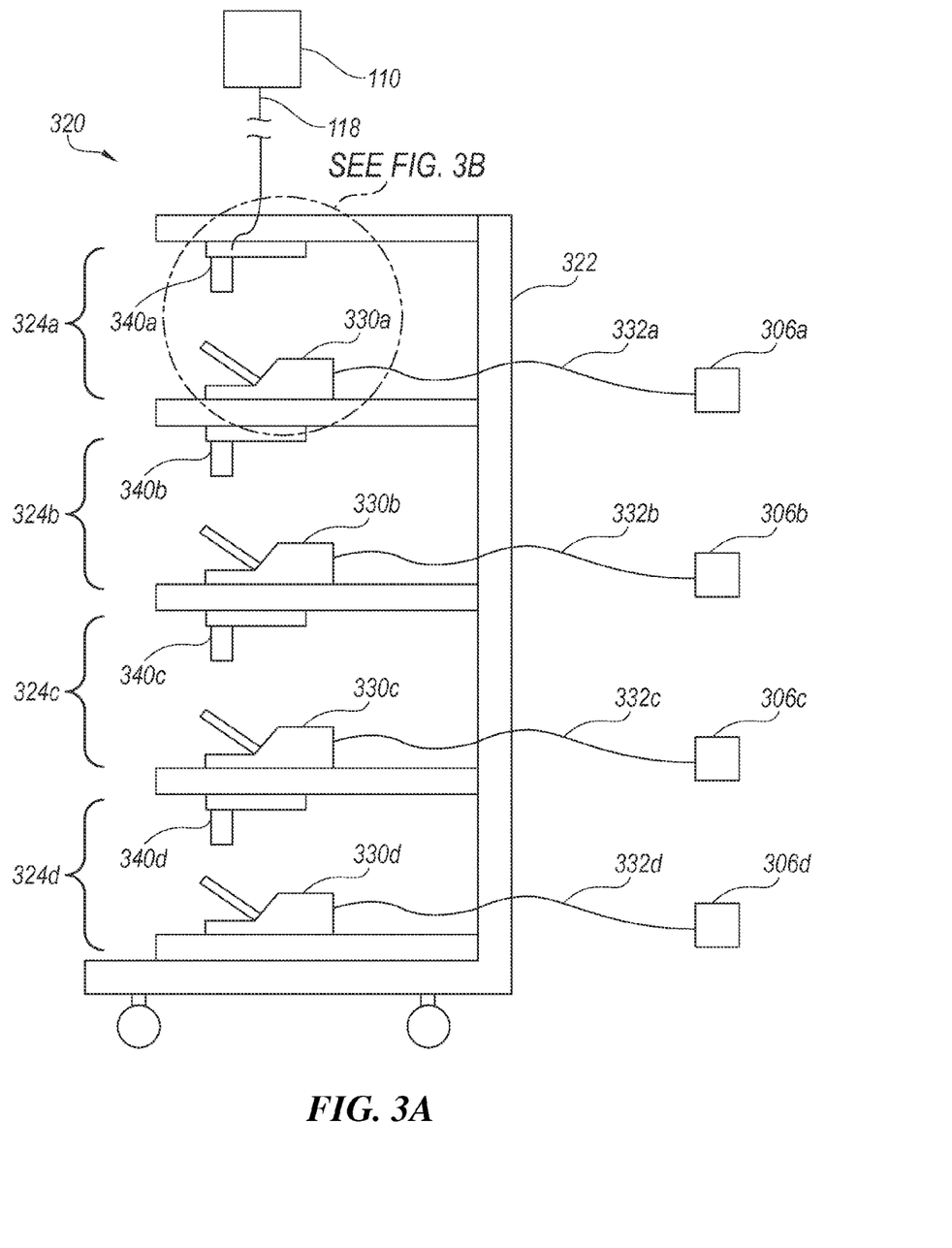
FIG. 3A is a side cutaway view an input device interface configured in accordance with still another embodiment of the present technology.

FIG. 3A is a partially schematic view of an input device interface or a hardware interface 320 (e.g., the second interface 220 of FIG. 1). The interface 320 includes an enclosure or housing 322 configured to hold or carry a plurality of containers, racks, shelves or modules 324 (identified separately as a first module 324a, a second module 324b, a third module 324c and a fourth module 324d). Individual modules 324 include a corresponding motor, mover or actuator 340 (identified separately as first actuator 340a, a second actuator 340b, a third actuator 340c and a fourth actuator 340d). The modules 324 are also sized or configured to receive one or more input devices 330 (identified separately as first input device 330a, a second device 330b, a third device 330c and a fourth device 330d). The input devices 330 (e.g., one or more of the input devices 130 from FIG. 1) can be connected or communicatively coupled via a link 332 (e.g., a wire, a cable and/or wireless transmission means) to a corresponding surgical instrument 306 (e.g., one of the surgical instruments 106 of FIG. 1). The link 118 communicatively couples the actuators 340 to the first interface 110.

Figure 3B:
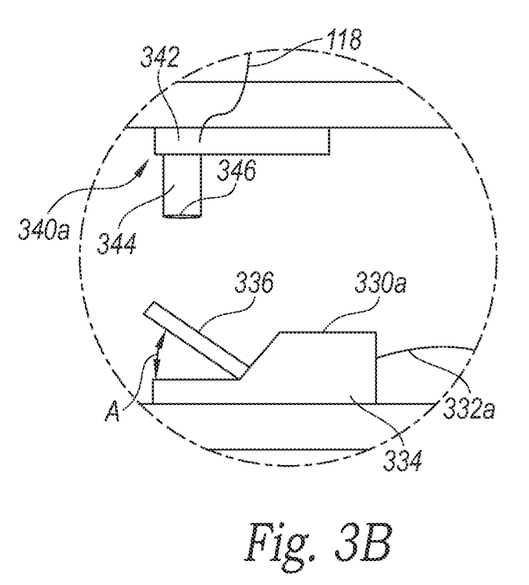
FIGS. 3B and 3C are enlarged views of a portion of FIG. 3A.
Figure 3C:
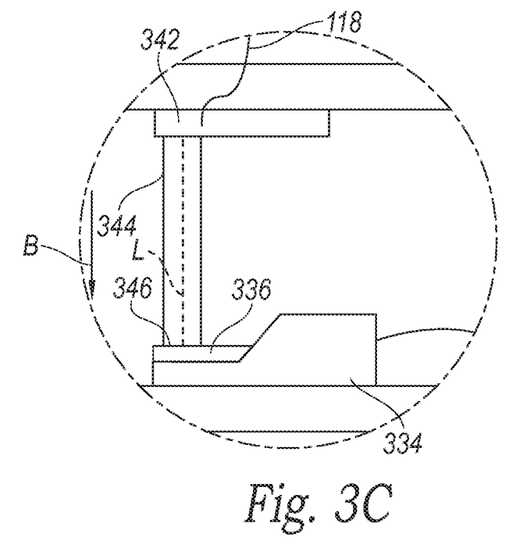

FIGS. 3B and 3C are enlarged cutaway views of a portion of FIG. 3A. Referring first to FIG. 3B, the first input device 330a includes a base portion 334 and a movable control surface or a pedal 336. In the illustrated embodiment of FIG. 3B, the movable control surface is in a first orientation that oriented at a first angle $\alpha$ (e.g., between about 10° and about 80° between about 20° and 70°, or between about 25° and 45°) and relative to the base portion 334 and oriented at a second angle (not shown) relative to the first actuator 340a. The first actuator 340a includes a base portion 342 coupled to a piston portion 344 having a distal end portion 346. As shown in FIG. 3C, when the first interface 110 receives input from an operator to activate the surgical instrument 306a (FIG. 3), the first interface 110 transmits instructions to the first actuator 340a via the link 118 to change the orientation of the pedal 336. As shown in FIG. 3C, the first actuator 340a correspondingly moves the distal end portion 346 toward the pedal 336 in a direction β generally parallel to a longitudinal axis of the piston portion 344. The pedal 336 in the second orientation (e.g., between about 0° and 20° relative to the base portion 334) provides a signal to the surgical instrument 306a via the link 332a to accordingly perform a predetermined task or action (e.g., assigned by the operator at the first interface 110). The interface 320 is therefore expected to provide automated control of a surgical instrument having an input device incapable (purposefully or otherwise) of direct connection to the first interface 110.

Figure 4:
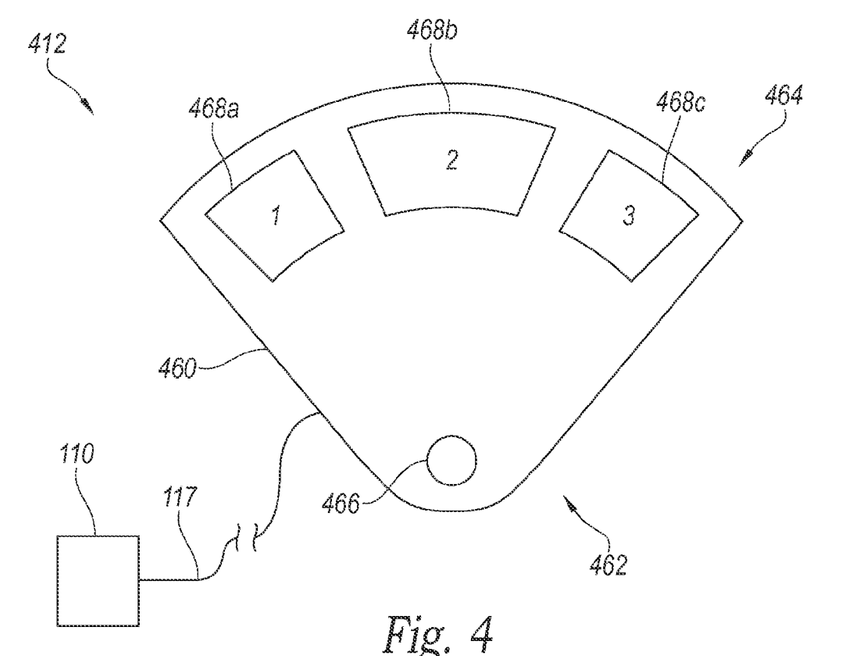
FIG. 4 is a schematic top view of an input surface configured in accordance with an embodiment of the present technology.

FIG. 4 is a schematic top view of an input 412 configured in accordance with embodiments with the present technology. The input 412 is communicatively coupled to the first interface 110 via the link 117 and can include an input surface 460 having a first end 462 extending to a second end 464. In the illustrated embodiment, the input surface 460 is configured to rest flat on a floor proximate an operating table (e.g., the operating table 102 of FIG. 1). In other embodiments, however, the input surface 460 be configured to be inclined relative to a floor near the operating table. A proximal input zone or region 466 can be configured to receive a first portion (e.g., a heel) of an operator's foot. A plurality of distal input zones or regions 468 (identified separately as a first region 468a, a second region 468b and a third region 468c) can be configured to receive input from a second end of the operator's foot different from the first portion of the foot. The regions 468 can be configured to receive, for example, touch and/or pressure input from the operator's foot. In some embodiments, the proximal region can be configured to operate as a switch or toggle configured to allow the user to select from multiple instruments or functions associated with individual regions 468. Moreover, in the illustrated embodiment of FIG. 4, the input 412 has a generally circular sector shape. In other embodiments, however, the input 412 can have any suitable shape, including, for example, a square, a rectangle, a circle, an ellipse, and/or a triangle.

Figure 5:
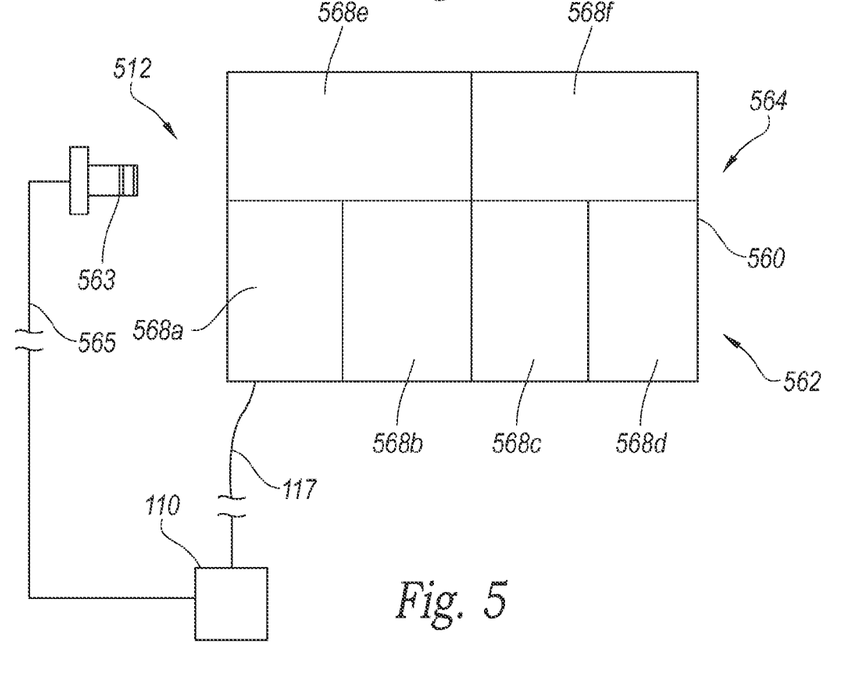
FIG. 5 is a schematic top view of an input surface configured in accordance with another embodiment of the present technology.

FIG. 5 is a schematic top view of an input 512 configured in accordance with an embodiment of the present technology. The input 512 includes a surface 560 having a first end 562 extending to a second end 564. The surface 560 includes a plurality of input zones 568, identified separately as a first input zone 568a, a second input zone 568b, a third input zone 568c, a fourth input zone 568d, a fifth input zone 568e and a sixth input zone 568f. Each of the input zones 568 can be selectively configured to be associated with one or more surgical instruments (e.g., the surgical instruments 106 of FIG. 1) by an operator. The operator, for example, can select one or more surgical instruments to be associated with one or more of the input zones 568 via the display 115 (FIG. 1). When the operator applies pressure to one of the input zones 568, a signal can be transmitted to the first interface 110 via the link 117 which can correspondingly communicate a signal to an input device coupled to the second interface 120 to activate the corresponding surgical instrument.

In some embodiments, for example, the input 512 can also include a camera 563 coupled to the first interface 110 via a link 565 (e.g., a wire, a cable and/or wireless transmission means). The camera 563 can be configured as a two-dimensional camera and/or three-dimensional camera that can track an operator's foot as she steps on the input 512. In other embodiments, for example, the input 512 can be reconfigured based on input received at the first interface 110. For example, the input 512 can be configured to have a reconfigurable color scheme such that the input zones 568 can have colors and/or patterns assigned by the first interface 110 based on the surgical instrument currently assigned to that input zone.

Figure 6:
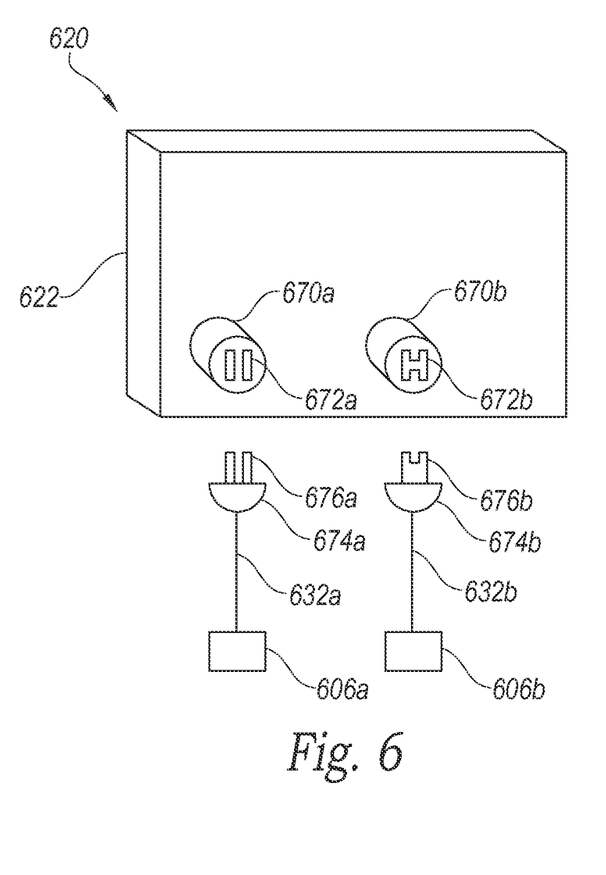
FIG. 6 is a partially schematic isometric rear view of an input device interface configured in accordance with still another embodiment of the present technology.

FIG. 6 is a partially schematic rear view of an interface 620 configured in accordance with an embodiment of the present technology. The interface 620 includes a housing 622 on which a plurality of receptacles 670 are disposed. The receptacles 670 are identified separately as a first receptacle 670a and a second receptacle 670b. The receptacles 670a and 670b can have input ports 672a and 672b, respectively. The input port 672a has a first shape different from a shape of the input port 672b such that the receptacles can receive inputs from two or more surgical instruments. For example, a first surgical instrument 606a and a second different surgical instrument 606b can be connected to first and second cables 632a and 632b, respectively, each having a plug 674 (identified separately as a first plug 674a and a second plug 674b). The first plug 674a has an end portion 676a different from an end portion 676b of the second plug 674b. In this way, the interface 620 having a plurality of the receptacles 670 can receive plugs from several different input devices provided by several different manufacturers such that the interface 620 can be connected or otherwise coupled to a variety of input devices or a variety of surgical instruments.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A surgical instrument input device organization system, comprising:
   a first interface configured to receive input from a user; and
   a second interface communicatively coupled to the first interface via a link, wherein the second interface includes a plurality of modules,
   wherein individual modules are sized to receive a surgical instrument input device, and
   wherein at least one of the plurality of modules includes an actuator configured to apply pressure to a movable surface of a surgical instrument input device in response to input received from the user at the first interface.

2. The system of claim 1 wherein the actuator includes an end portion configured to engage the movable surface with a predetermined amount of pressure to change an orientation of the movable surface relative to the end portion of the actuator from between a first orientation and at least a second orientation, and wherein the input device is configured to selectively activate and deactivate a surgical instrument communicatively coupled thereto based on the orientation of the movable surface.

3. The system of claim 1 wherein the movable surface comprises a pedal.

4. The system of claim 1 wherein the second interface further includes one or more receptacles, wherein individual receptacles are sized to receive a plug electrically connected to a surgical instrument input device.

5. The system of claim 4 wherein:
   the one or more receptacles include a first receptacle and a second receptacle having first and second input ports, respectively;
   the first input port is sized to receive a first plug from a first surgical instrument input device; and
   the second input port is sized to receive a second plug from a second surgical instrument input device different from the first input device.

6. The system of claim 1 wherein the first interface comprises a first surface configured to receive input from a foot of the user.

7. The system of claim 6 wherein the first surface has a proximal portion configured to receive a first portion of the user's foot and a plurality of distal portions configured to receive touch input from an a second, different portion of the user's foot.

8. The system of claim 6 wherein the first surface has a circular sector shape.

9. The system of claim 6 wherein the first surface comprises a first input surface and a second input surface, wherein the first and second input surfaces are configured to selectively activate and deactivate first and second surgical instruments, respectively, based on input from the user's foot.

10. The system of claim 1 wherein the first interface includes a camera configured to track a position of at least a portion of a foot of the user.

11. A surgical instrument input device organization system, comprising:
    an input/output system configured to receive input from an operator; and
    an enclosure configured to hold a plurality of modules, wherein individual modules are configured to receive a surgical instrument input device,
    wherein individual modules include an actuator communicatively coupled to the input/output system and positioned at least proximate a corresponding surgical instrument input device, and
    wherein the actuator is configured to displace a movable surface of a surgical instrument input device in response to input received from the operator.

12. The system of claim 11 wherein the movable surface includes a pedal, and wherein the actuator is configured to engage the pedal with a predetermined amount of pressure to move the pedal from a first orientation to a second orientation, and further wherein the input device is configured to provide an operating instruction to a surgical instrument communicatively coupled thereto when the pedal is in the second orientation.

13. The system of claim 11 wherein the input/output system comprises a first surface configured to receive input from a foot the operator.

14. The system of claim 13 wherein the first surface has a proximal portion configured to receive a first portion of the operator's foot and a plurality of distal portions configured to receive touch input from a second, different portion of the operator's foot.

15. The system of claim 14 wherein:
    the input/output system comprises a first input surface and a second input surface selectively associated with first and second surgical instruments, respectively; and
    the first and second input surfaces are configured to selectively activate and deactivate the first and second surgical instruments, respectively, based on input received from the operator.

16. The system of claim 13 wherein:
    the first surface includes a plurality of input zones selectively associated with corresponding surgical instruments; and
    individual input zones are configured to receive input from the operator's foot and selectively activate and deactivate an actuator positioned proximate a surgical instrument input device coupled to a corresponding surgical instrument.

17. The system of claim 11 wherein the input/output system includes at least one of a touchscreen configured to present a graphical user interface to the operator, a microphone configured to receive voice input from the operator and a pressure-sensitive surface configured to receive foot input from the operator.

18. A surgical instrument input device organization system, comprising:
    means for receiving input from a clinician;
    means for applying pressure to a pedal of an input device coupled to a surgical instrument, wherein the means for applying pressure is positioned remote from both the means for receiving input and the surgical instrument; and
    a link configured to communicatively couple the means for receiving input to the means for applying pressure, wherein the means for applying pressure is configured change an orientation of the pedal from between a first orientation and a second orientation in response to input received from the clinician via the link.

19. The system of claim 18, further comprising a housing sized and shaped to hold the means for applying pressure and at least one input device.

20. The system of claim 18 wherein the means for receiving input from the clinician's foot is configured to distinguish between a dorsiflexion and plantar flexion of a clinician's foot.

21. The system of claim 18 wherein the means for receiving input from the clinician's foot is configured to distinguish between pronation and supination of a clinician's foot.

22. The system of claim 18 wherein the means for receiving input from the clinician's foot is configured to distinguish between inversion and eversion of a clinician's foot.

23. The system of claim 18 wherein the means for receiving input comprises means for tracking one or more movements of at least one of a clinician's hands.

24. A surgical instrument input device organization system, comprising:
- an interface configured to receive input from a clinician;
- an actuator configured to apply pressure to a pedal of an input device coupled to a surgical instrument, wherein the actuator is positioned remote from both the interface and the surgical instrument; and
- a link configured to communicatively couple the interface and the actuator, wherein the actuator is configured change an orientation of the pedal between a first orientation and a second orientation in response to input received from the clinician via the link.

* * * * *

UNITED STATES PATENT AND TRADEMARK OFFICE
CERTIFICATE OF CORRECTION

PATENT NO. : 9,498,194 B2  Page 1 of 1
APPLICATION NO. : 14/255779
DATED : November 22, 2016
INVENTOR(S) : Kristen S. Moe et al.

It is certified that error appears in the above-identified patent and that said Letters Patent is hereby corrected as shown below:

In the Specification

In Column 2, Line 25, delete "an a" and insert -- a --, therefor.

In Column 8, Line 66, delete "α" and insert -- A --, therefor.

In Column 9, Line 11, delete "β" and insert -- B --, therefor.

In the Claims

In Column 11, Line 46, in Claim 7, delete "an a" and insert -- a --, therefor.

In Column 12, Line 17, in Claim 13, after "foot" insert -- of --.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*